(12) United States Patent
Gane et al.

(10) Patent No.: US 7,241,921 B2
(45) Date of Patent: Jul. 10, 2007

(54) BACTERIAL ENZYME INHIBITORS

(75) Inventors: Paul Gane, Cambridge (GB); Barry Porter, Cambridge (GB); Henriette Willems, Cambridge (GB); Raymond Paul Beckett, Oxford (GB); Kenneth Keavey, Oxford (GB)

(73) Assignee: De Novo Pharmaceuticals Limited (GB)

( * ) Notice: Subject to any disclaimer, the term of this patent is extended or adjusted under 35 U.S.C. 154(b) by 319 days.

(21) Appl. No.: 10/497,494

(22) PCT Filed: Nov. 27, 2002

(86) PCT No.: PCT/GB02/05350

§ 371 (c)(1),
(2), (4) Date: Feb. 23, 2005

(87) PCT Pub. No.: WO03/048115

PCT Pub. Date: Jun. 12, 2003

(65) Prior Publication Data

US 2005/0159412 A1    Jul. 21, 2005

(30) Foreign Application Priority Data

Dec. 4, 2001    (GB) .................. 0128943.8

(51) Int. Cl.
*C07C 259/04*    (2006.01)
*A61K 31/19*    (2006.01)
(52) U.S. Cl. ..................................... 562/621; 562/623
(58) Field of Classification Search ............ 514/227.5, 514/357, 237.5, 575, 255.01; 562/621, 623; 544/59, 159, 102; 546/184, 329; 548/138, 548/146, 143, 215
See application file for complete search history.

(56) References Cited

U.S. PATENT DOCUMENTS 4,025,622 A    5/1977    Ogura et al.

FOREIGN PATENT DOCUMENTS

WO    WO 99 39704    8/1999
WO    WO 99 59568    11/1999

OTHER PUBLICATIONS

Chen et al: "Actinonin, a naturally occurring antibacterial agent, is a potent deformylase inhibitor" Biochemistry, American Chemical Society. Easton, PA, US, vol. 39, Feb. 15, 2000, pp. 1256-1262, XP002158085 ISSN: 0006-2960.

*Primary Examiner*—Shailendra Kumar
(74) *Attorney, Agent, or Firm*—Banner & Witcoff, Ltd.

(57) ABSTRACT

Compounds of formula (I) are antibacterial agents: wherein: Z is —N(OH)CH(=O) or —C(=O)NH(OH); $R_1$ represents hydrogen, methyl or trifluoromethyl or, except when Z is a radical of formula —N(OH)CH(=O), a hydroxy, halo or amino group; $R_2$, $R_3$ and $R_4$ independently represents hydrogen or a group $R_{10}$—$(D)_n$—$(ALK)_m$— wherein $R_{10}$, D, n, m and ALK are as defined in the claims; or $R_3$ and $R_4$ taken together with the nitrogen atom to which they are attached form an optionally substituted monocyclic heterocyclic ring containing from 5 to 7 ring atoms, one of which is the nitrogen atom to which $R_4$ and $R_5$ are attached and the remaining ring atoms being selected from compatible combinations of carbon, oxygen, sulfur and nitrogen (I)

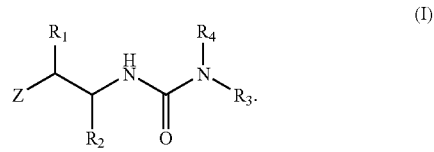

12 Claims, No Drawings

BACTERIAL ENZYME INHIBITORS

This application is a U.S. National Stage application of co-pending PCT application PCT/GB02/05350 filed 27 Nov. 2002, which claims the priority of United Kingdom Patent Application No. 0128943.8 filed 4 Dec., 2001. These applications are incorporated herein by reference in there entireties.

This invention relates to hydroxamic acid and N-formyl hydroxylamine compounds which inhibit the activity of the bacterial enzyme known as peptide deformylase. Since bacterial growth is known to be inhibited by inhibitors of peptide deformylase, the compounds of the invention are expected to include antibacterial agents.

BACKGROUND TO THE INVENTION

The compounds of the invention are inhibitors of bacterial polypeptide deformylase (PDF; EC 3.5.1.31).

All ribosome-mediated synthesis of proteins starts with a methionine residue. In prokaryotes, the methionyl moiety carried by the initiator tRNA is N-formylated prior to its incorporation into a polypeptide. Consequently, N-formyl-methionine is always present at the N-terminus of a nascent bacterial polypeptide. However, most mature proteins do not retain the N-formyl group or the terminal methionine residue. Deformylation is required prior to methionine removal, since methionine aminopeptidase does not recognise peptides with an N-terminal formylmethionine residue (Solbiati et al., J. Mol. Biol. 290: 607–614, 1999). Deformylation is, therefore, a crucial step in bacterial protein biosynthesis and the enzyme responsible, PDF, is essential for normal bacterial growth. The gene encoding PDF (def) is present in all pathogenic bacteria for which sequences are known (Meinnel et al., J. Mol. Biol, 266: 939–49, 1997). Although a deformylase homologue has recently been cloned from the mitochondria of human cells (Giglione et. el. EMBO Journal, 19, 5916–5929, 2000) it has not been shown to be functional, and its relevance is unknown. Since a number of currently used antibiotics are known to act on both bacteria and mitochondria, PDF is still considered to be a target for antibacterial chemotherapy (for a review see Giglione et al., Mol Microbiol., 36: 1197–1205, 2000).

The isolation and characterisation of PDF has been facilitated by an understanding of the importance of the metal ion in the active site (Groche et al., Biophys. Biochem. Res. Commun., 246: 324–6, 1998). The $Fe^{2+}$ form is highly active in vivo but is unstable when isolated due to oxidative degradation (Rajagopalan et al., J. Biol. Chem. 273: 22305–10, 1998). The $Ni^{2+}$ form of the enzyme has specific activity comparable with the ferrous enzyme but is oxygen-insensitive (Ragusa et al., J. Mol. Biol. 1998, 280: 515–23, 1998). The $Zn^{2+}$ enzyme is also stable but is almost devoid of catalytic activity (Rajagopalan et al., J. Am. Chem. Soc. 119: 12418–12419, 1997).

Several X-ray crystal structures and NMR structures of *E. coli* PDF, with or without bound inhibitors, have been published (Chan et al., Biochemistry 36: 13904–9, 1997; Becker et al., Nature Struct. Biol. 5: 1053–8, 1998; Becker et al., J. Biol. Chem. 273: 11413–6, 1998; Hao et al., Biochemistry, 38: 4712–9, 1999; Dardel et al., J. Mol. Biol. 280: 501–13, 1998; O'Connell et al., J. Biomol. NMR, 13: 311–24, 1999), indicating similarities in active site geometry to metalloproteinases such as thermolysin and the metzincins.

The substrate specificity of PDF has been extensively studied (Ragusa et al., J. Mol. Biol. 289: 1445–57, 1999; Hu et al., Biochemistry 38: 643–50, 1999; Meinnel et al., Biochemistry, 38: 4287–95, 1999). These authors conclude that an unbranched hydrophobic chain is preferred at P1', while a wide variety of P2' substituents are acceptable and an aromatic amide substituent may be advantageous at the P3' position. There have also been reports that small peptidic compounds containing an H-phosphonate (Hu et al., Bioorg. Med. Chem. Lett., 8: 2479–82, 1998) or thiol (Meinnel et al., Biochemistry, 38: 4287–95, 1999; Huntingdon et al., Biochemistry, 39: 4543–51, 2000; Wei et al, J. Combinatorial Chem., 2: 650–57, 2000) metal binding group are micromolar inhibitors of PDF. Peptide aldehydes such as calpeptin (N-Cbz-Leu-norleucinal) have also been shown to inhibit PDF (Durand et al., Arch. Biochem. Biophys., 367: 297–302, 1999). Recently, the naturally occurring hydroxamic acid antibiotic actinonin, for which the target of its antibacterial activity was previously unknown, was shown to be a potent inhibitor of polypeptide deformylase (WO 99/39704, and Chen et al, Biochemistry, 39: 1256–62, 2000). Examples of non-peptidic PDF inhibitors with carboxylic acid (Green et al., Arch. Biochem. Biophys. 375: 355–8, 2000; Jayasekera et al., ibid., 381: 313–6, 2000) or hydroxamic acid (Apfel et al., J. Med. Chem., 43: 2324–31, 2000) metal binding groups are also known.

It has been reported that PDF is present in eukaryotic parasites such as *Plasmodium falciparum* (Meinnel, Parasitology Today, 16: 165–8, 2000). Those authors also found evidence for the presence of PDF in other parasites of humans, such as the kinetoplastid protozoan parasites *Trypanosoma brucei* and *Leishmania major*. Based on these findings, it is anticipated that the hydroxamic acid and N-formyl hydroxylamine compounds with which this invention is concerned have antiprotozoal activity, and are useful in the treatment of malaria and other protozoal diseases.

Several patent applications describe antibacterial hydroxamic acid and N-formyl hydroxylamine agents whose activity has been attributed to inhibition of PDF. These publications include our copending International patent applications nos. WO 99/39704, WO 99/59568, WO 00/35440, WO 00/44373, WO 00/58294 and WO 00/61134, as well as WO 01/40198 (Aventis), WO 01/44179 (Versicor), WO 01/44178 (Versicor), and WO 01/38561 (Questcor).

Further, actinonin is a naturally occurring antibacterial agent having a hydroxamic acid group, and certain derivatives of actinonin are also known to have antibacterial activity. (see for example Bouboutou et al, Colloq. INSERM (1989) 174 (Forum Pept. $2^{nd}$, 1988), 341–4; Lelevre et. al. Pathol. Biol. (1989), 37(1), 43–46; Broughton et. al. J. Chem. Soc. Perkin Trans. 1 (1975) (9), 857–60. The antibacterial activity of actinonin has been shown to be due, at least in part, to inhibition of PDF (WO 99/39704 and other publications).

BRIEF DESCRIPTION OF THE INVENTION

This invention is based on the discovery of a class of hydroxamic acid and N-formyl hydroxylamine derivatives which are inhibitors of the activity of PDF. Compounds in that class are therefore expected to have antibacterial activity. The class includes novel structures which form part of the invention. Also within the scope of the invention is a method of identifying antibacterial agents from within the class of PDF inhibitors of the invention.

DETAILED DESCRIPTION OF THE INVENTION

According to the invention there is provided a compound of formula (I), or a salt or hydrate thereof:

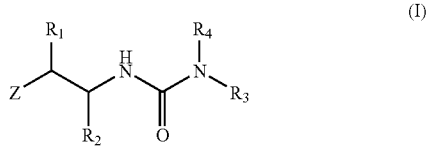

wherein:
Z represents a radical of formula —N(OH)CH(═O) or formula —C(═O)NH(OH);
$R_1$ represents hydrogen, methyl or trifluoromethyl or, except when Z is a radical of formula —N(OH)CH(═O), a hydroxy, halo or amino group
$R_2$ represents hydrogen or a group $R_{10}$—$(D)_n$—$(ALK)_m$— wherein
   $R_{10}$ represents an optionally substituted $C_1$–$C_6$ alkyl, $C_2$–$C_6$ alkenyl, $C_2$–$C_6$ alkynyl, cycloalkyl, aryl, or heterocyclyl group and
   ALK represents a straight or branched divalent $C_1$–$C_6$ alkylene, $C_2$–$C_6$ alkenylene, or $C_2$–$C_6$ alkynylene radical, and may be interrupted by one or more non-adjacent —NH—, —O— or —S— linkages,
   D represents —NH—, —O— or —S—, and
   n is 0 or 1;
$R_3$ and $R_4$ independently represent hydrogen or a group $R_{10}$—$(D)_n$—$(ALK)_m$— as defined for $R_2$, or
$R_3$ and $R_4$ taken together with the nitrogen atom to which they are attached form an optionally substituted monocyclic heterocyclic ring containing from 5 to 7 ring atoms, one of which is the nitrogen atom to which $R_4$ and $R_5$ are attached and the remaining ring atoms being selected from compatible combinations of carbon, oxygen, sulfur and nitrogen.

In another aspect, the invention provides a method for the treatment of bacterial infections in humans and non-human mammals, which comprises administering to a subject suffering such infection an antibacterially effective dose of a compound of formula (I) as defined above.

In a further aspect of the invention there is provided a method for the treatment of bacterial contamination by applying an antibacterially effective amount of a compound of formula (I) as defined above to the site of contamination.

The compounds of formula (I) as defined above may be used as component(s) of antibacterial cleaning or disinfecting materials.

As used herein the term "($C_1$–$C_6$)alkyl" means a straight or branched chain alkyl moiety having from 1 to 6 carbon atoms, including for example, methyl, ethyl, n-propyl, isopropyl, n-butyl, isobutyl, sec-butyl, t-butyl, n-pentyl and n-hexyl.

As used herein the term "($C_2$–$C_6$)alkenyl" means a straight or branched chain alkenyl moiety having from 2 to 6 carbon atoms having at least one double bond of either E or Z stereochemistry where applicable. The term includes, for example, vinyl, allyl, 1- and 2-butenyl and 2-methyl-2-propenyl.

As used herein the term "$C_2$–$C_6$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "cycloalkyl" means a saturated alicyclic moiety having from 3–8 carbon atoms and includes, for example, cyclopropyl, cyclobutyl, cyclopentyl, cyclohexyl, cycloheptyl and cyclooctyl.

As used herein the term "aryl" refers to a mono-, bi- or tri-cyclic carbocyclic aromatic group, and to groups consisting of two covalently linked monocyclic carbocyclic aromatic groups. Illustrative of such groups are phenyl, biphenyl and napthyl.

As used herein the term "heteroaryl" refers to a 5- or 6-membered aromatic ring containing one or more heteroatoms; Illustrative of such groups are thienyl, furyl, pyrrolyl, imidazolyl, benzimidazolyl, thiazolyl, pyrazolyl, isoxazolyl, isothiazolyl, triazolyl, thiadiazolyl, oxadiazolyl, pyridinyl, pyridazinyl, pyrimidinyl, pyrazinyl, triazinyl.

As used herein the unqualified term "heterocyclyl" or "heterocyclic" includes "heteroaryl" as defined above, and in particular means a 5–7 membered aromatic or non-aromatic heterocyclic ring containing one or more heteroatoms selected from S, N and O, including for example, pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzofuranyl, pyranyl, isoxazolyl, benzimidazolyl, methylenedioxyphenyl, maleimido and succinimido groups.

Unless otherwise specified in the context in which it occurs, the term "substituted" as applied to any moiety herein means substituted with up to four substituents, each of which independently may be ($C_1$–$C_6$)alkyl, phenyl, benzyl, ($C_1$–$C_6$)alkoxy, hydroxy, mercapto, ($C_1$–$C_6$)alkylthio, amino, halo (including fluoro, chloro, bromo and iodo), cyano, trifluoromethyl, nitro, —COOH, —CONH$_2$, —COR$^A$, —COOR$^A$, —NHCOR$^A$, —CONHR$^A$, —NHR$^A$, —NR$^A$R$^B$, or —CONR$^A$R$^B$ wherein R$^A$ and R$^B$ are independently a ($C_1$–$C_6$)alkyl group. In the case where the substituent is phenyl or benzyl, the phenyl ring may be substituted with any of the foregoing except phenyl or benzyl.

There are several actual or potential chiral centres in the compounds according to the invention because of the presence of asymmetric carbon atoms. The presence of several asymmetric carbon atoms gives rise to a number of diastereoisomers with R or S stereochemistry at each chiral centre. The invention includes all such diastereoisomers and mixtures thereof. Currently, the preferred stereoconfiguration of the carbon atom carrying the $R_2$ group is R; and that of the carbon atom carrying the $R_1$ group (when asymmetric) is R.

In the compounds of the invention:
When Z is a radical of formula —N(OH)CH(═O), $R_1$ is hydrogen, methyl or trifluoromethyl. When Z is a radical of formula —C(═O)NH(OH), $R_1$ is hydrogen, methyl, trifluoromethyl, hydroxy, halo (e.g. chloro, bromo or especially fluoro) or amino. Hydrogen is currently preferred in both cases.

$R_2$ may be, for example:
   optionally substituted $C_1$–$C_8$ alkyl, $C_3$–$C_6$ alkenyl, $C_3$–$C_6$ alkynyl or cycloalkyl;
   phenyl($C_1$–$C_6$ alkyl)-, phenyl($C_3$–$C_6$ alkenyl)- or phenyl ($C_3$–$C_6$ alkynyl)- optionally substituted in the phenyl ring;
   cycloalkyl($C_1$–$C_6$ alkyl)-, cycloalkyl($C_3$–$C_6$ alkenyl)- or cycloalkyl($C_3$–$C_6$ alkynyl)-optionally substituted in the cycloalkyl ring;

heterocyclyl($C_1$–$C_6$ alkyl)-, heterocyclyl($C_3$–$C_6$ alkenyl)- or heterocyclyl($C_3$–$C_6$ alkynyl)- optionally substituted in the heterocyclyl ring; or $CH_3(CH_2)_pO(CH_2)_q$— or $CH_3(CH_2)_pS(CH_2)_q$—, wherein p is 0, 1, 2 or 3 and q is 1, 2 or 3.

Specific examples of $R_2$ groups include methyl, ethyl, n- and iso-propyl, n- and iso-butyl, n-pentyl, iso-pentyl 3-methyl-but-1-yl, n-hexyl, n-heptyl, n-octyl, methylsulfanylethyl, ethylsulfanylmethyl, 2-methoxyethyl, 2-ethoxyethyl, ethoxymethyl, 3-hydroxypropyl, allyl, 3-phenylprop-3-en-1-yl, prop-2-yn-1-yl, 3-phenylprop-2-yn-1-yl, 3-(2-chlorophenyl)prop-2-yn-1-yl, but-2-yn-1-yl, cyclopentyl, cyclohexyl, cyclopentylmethyl, cyclopentylethyl, cyclopentylpropyl, cyclohexylmethyl, cyclohexylethyl, cyclohexylpropyl, furan-2-ylmethyl, furan-3-ylmethyl, tetrahydrofuran-2-ylmethyl, tetrahydrofuran-2-ylmethyl, piperidinylmethyl, phenylpropyl, 4-chlorophenylpropyl, 4-methylphenylpropyl, 4-methoxyphenylpropyl, benzyl, 4-chlorobenzyl, 4-methylbenzyl, and 4-methoxybenzyl.

Presently preferred groups at $R_2$ are ($C_1$–$C_6$)alkyl-, cycloalkylmethyl-, ($C_1$–$C_3$) alkyl-S—($C_1$–$C_3$)alkyl-, or ($C_1$–$C_3$)alkyl-O—($C_1$–$C_3$)alkyl-, especially n-propyl, n-butyl n-pentyl, cyclopentylmethyl, cyclopentylethyl, cyclohexylmethyl or cyclohexylethyl.

$R_3$ may be any of the groups discussed in relation to $R_2$, but presently it is preferred that $R_3$ is hydrogen.

Examples of groups $R_4$ are methyl, ethyl, n- and iso-propyl, n- and iso-butyl, n-pentyl, iso-pentyl, 3-methyl-but-1-yl, n-hexyl, n-heptyl, n-octyl, hydroxymethyl, 2-hydroxymethyl, methoxymethyl, 2-methoxyethyl, 2-ethoxyethyl, 2-ethoxymethyl, 3-hydroxypropyl, allyl, cyclopentyl, cyclohexyl, cyclopentylmethyl, cyclopentylethyl, cyclopentylpropyl, cyclohexylmethyl, cyclohexylethyl, cyclohexylpropyl, furan-2-ylmethyl, furan-3-methyl, tetrahydrofuran-2-ylmethyl, tetrahydrofuran-2-ylmethyl, piperidinyl, piperazinyl, piperidinylmethyl, piperazinylmethyl, phenyl, 4-chlorophenyl, 4-methylphenyl 4-methoxyphenyl, 4-hydroxyphenyl, 4-aminophenyl, benzyl, 4-chlorobenzyl, 4-methylbenzyl, 4-methoxybenzyl, 4-hydroxybenzy, 4-aminobenzyl, naphthyl, naphthylmethyl and naphthyl and naphthylmethyl substituted in the naphthyl rings by methyl, methoxy, hydroxy, chloro, or amino.

When $R_3$ and $R_4$ taken together with the nitrogen to which they are attached form a heterocyclic ring, that ring may be, for example piperidino, piperazino, morpholino, pyridyl, oxazolyl, thiazolyl, oxadiazolyl, or thiadiazolyl, any of which may be substituted, for example by methyl, methoxy, hydroxy, chloro, or amino.

Specific examples of compounds of the invention include

N-hydroxy-N-[2R-(3-naphthalen-1-ylmethyl-ureido)-hexyl]-formamide,

N-[2R-(3-Benzyl-ureido)-hexyl]-N-hydroxy-formamide,

N-{3-Cyclopentyl-2R-[3-(3,4-dimethoxy-benzyl)-ureido]-propyl}-N-hydroxy-formamide, N-{3-Cyclopentyl-2R-[3-pyridin-4-ylmethyl-ureido)-propyl]-N-hydroxy-formamide, N-{3-Cyclopentyl-2R-[3-(4-methoxy-benzyl)-ureido]-propyl-N-hydroxy-formamide, N-{3-Cyclopentyl-2R-[3-(4-methoxy-benzyl)-ureido]-propyl-N-hydroxy-formamide and 4-Phenyl-piperazine-1-carboxylic acid[1R-cyclopentylmethyl-2-(formyl-hydroxy-amino)-ethyl]-amide as well as the corresponding compounds in which the N-hydroxy formylamino group is replaced by a hydroxamic acid group.

Compounds of the invention in which Z is an N-formylhydroxyamino group may be prepared by deprotecting an O-protected N-formyl-N-hydroxyamino compound of formula (II):

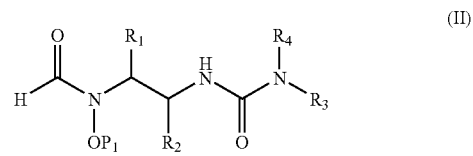

(II)

in which $R_1$, $R_2$, $R_3$, and $R_4$ are as defined for general formula (I) and $P_1$ is a hydroxy protecting group removable to leave a hydroxy group by hydrogenolysis or hydrolysis. Benzyl is a preferred $P_1$ group for removal by hydrogenolysis, and tert-butyl and tetrahydropyranyl are preferred groups for removal by acid hydrolysis.

Compounds of formula (II) may be prepared by reaction of a compound of formula (IVA)

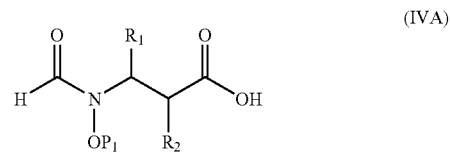

(IVA)

with diphenylphosphoryl azide to form an intermediate compound of formula (IVB)

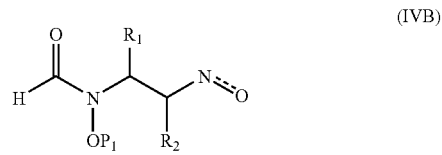

(IVB)

then reacting compound (IVB) with an amine of formula $R_3R_4NH$.

Compounds of formula (II) may also be prepared by N-formylation, for example using acetic anhydride and formic acid, or 1-formylbenzotriazole, of compounds of formula (III)

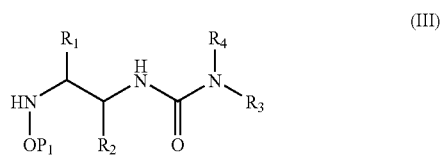

(III)

wherein $R_1$, $R_2$, $R_3$ and $R_4$ and $P_1$ are as defined in relation to formula (II).

Compounds (III) may be prepared by reaction of a carboxylic acid of formula (IV)

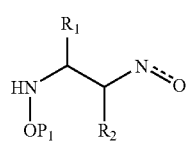
(IV)

with diphenylphosphoryl azide to form an intermediate compound of formula (IVC)

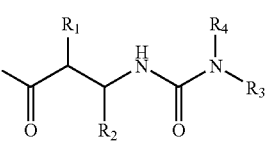
(IVC)

then reacting compound (IVC) with an amine of formula $R_3R_4NH$.

Compounds of the invention in which Z is a hydroxamic acid group may be prepared by reacting the parent compound wherein Z is a carboxylic acid group (IIA)

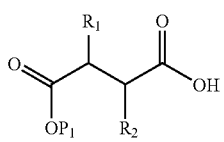
(IIA)

with hydroxylamine or an N- and/or O-protected hydroxylamine, and thereafter removing any O- or N-protecting groups.

Compounds of formula (IIA) may be prepared by reaction of a carboxylic acid of formula (V)

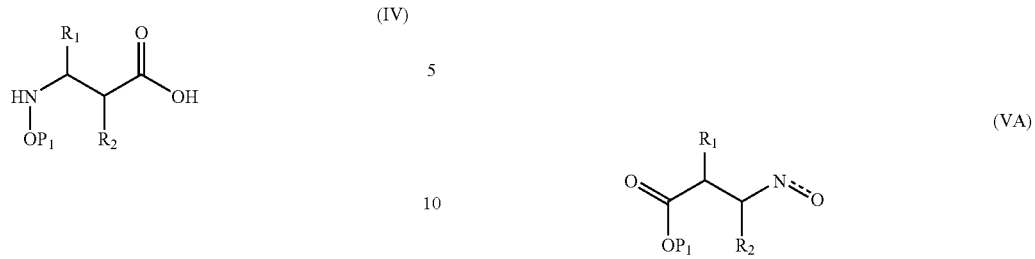
(V), (VA)

with diphenylphosphoryl azide to form an intermediate compound of formula (VA)

then reacting compound (VA) with an amine of formula $R_3R_4NH$, then removing the protecting group $P_1$.

Further details of the preparation of compounds of the invention are presented in the following Example, wherein the following abreviations are used:

| | |
|---|---|
| Bn | Benzyl |
| DPPA | Diphenylphosphoryl azide |
| HPLC | High performance liquid chromatography |
| LRMS | Low resolution mass spectrometry |
| RT | Retention time |
| TFA | Trifluoroacetic acid |

Analytical HPLC was run on a Beckman System Gold, using Waters Symmetry C18 column (50 mm, 4.6 mm) with 20 to 90% solvent B gradient (1.5 ml/min) as the mobile phase. [Solvent A: 0.05% TFA in 10% water 90% MeCN; Solvent B: 0.05% TFA in 10% MeCN 90% water, 5 min gradient time], detection wavelength at 214 nm. Preparative HPLC was run on a Gilson autoprep instrument using a C18 Waters delta pak (15 μm, 300 A, 25 mm, 10 mm) with 20 to 90% solvent B gradient (6 ml/min) as the mobile phase. [Solvent A 10% MeCN/water; Solvent B: 10% water/MeCN, 13 min gradient time], UV detection was at 214 nm. Reagents were purified and dried where necessary by standard techniques.

EXAMPLE 1

The preparation of N-hydroxy-N-[2R-(3-naphthalen-1-ylmethyl-ureido)-hexyl]-formamide is outlined in Scheme 1. 2R-[(Benzyloxy-formyl-amino)-methyl]-hexanoic acid was prepared by analogy with methods in international patent application WO 99/39704.

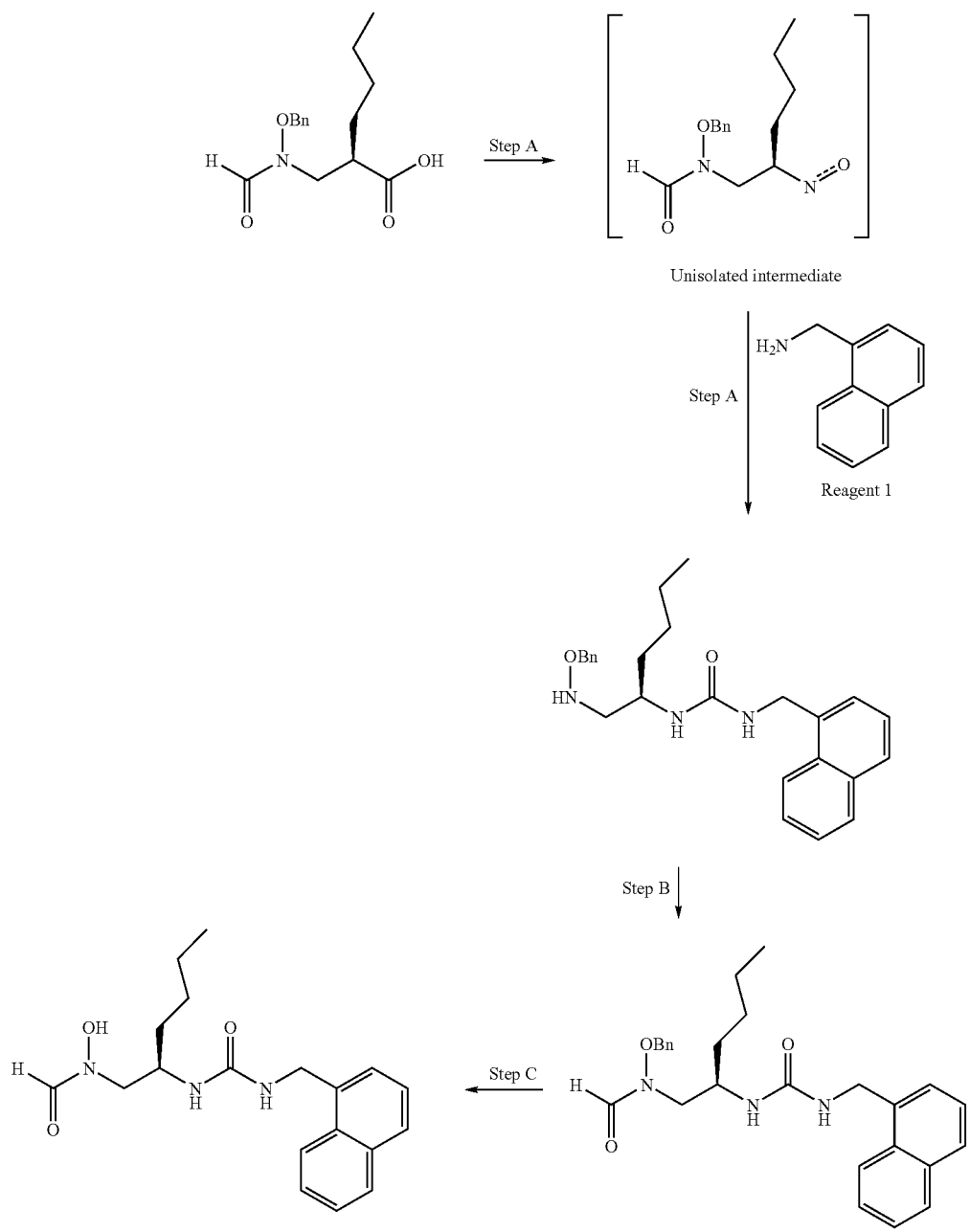

Reagents and Conditions: A. DPPA, Et₃N, reagent 1, toluene, heat 80° C.; B. Formyl-acetic anhydride, CH₂Cl₂, Et₃N; C. H₂, Pd/C, EtOH

Step A: 1-[1R-(benzyloxyamino-methyl)-pentyl]-3-naphthalen-1-ylmethyl-urea

A mixture of 2R-[(benzyloxy-formyl-amino)-methyl]-hexanoic acid (360 mg, 1.3 mmol), DPPA (273 µl, 1.3 mmol) and triethylamine (180 µl, 1.3 mmol) in a solution of toluene (12 ml) were heated to 80° C. After 0.5 h 1-naphthylmethylamine (433 µl, 2.6 mmol) was added and the reaction mixture was stirred for 18 h at 80° C. The mixture was allowed to cool and the solvent was removed in vacuo to yield an oily residue which was taken up in dichloromethane (20 ml). The organic phase was washed with 1M hydrochloric acid (2×20 ml), 1M sodium carbonate (2×20 ml), brine (1×20 ml), dried over anhydrous magnesium sulphate and the solvent was removed in vacuo to yield 1.0 g of a brown oil. Flash chromatography (dichloromethane, 3% methanol) yielded the title compound as a cloudy oil (100 mg, 18%). LRMS +ve: 406 (M+1, 100%). HPLC: RT 5.8 min (100%); $^1$H-NMR (CDCl₃) δ: 8.04 (1H, d, J=8.1 Hz), 7.88–7.84 (1H, m), 7.77–7.75 (1H, m), 7.52–7.47 (2H, m), 7.39–7.13 (7H, m), 5.72 (1H, brs), 5.15 (1H, brs), 4.77 (2H, d, J=5.3 Hz), 4.40–4.38 (3H, m) 3.69 (1H, s), 2.98 (1H, dd, J=13.5 & 2.8 Hz), 2.70–2.66 (1H, m), 1.42–1.22 (6H, m), 0.95(3H, t, J 12.5 Hz).

Step B: N-Benzyloxy-N-[2R-(3-naphthalen-1-ylm-ethyl-ureido)-hexyl]-formamide

To a solution of 1-[1R-(benzyloxyamino-methyl)-pentyl]-3-naphthalen-1-ylmethyl-urea (94 mg, 0.24 mmol) in dichloromethane (5 ml) was added formyl-acetic anhydride (63 ul, 0.72 mmol) and triethylamine (99 μl, 0.72 mmol) and the reaction mixture was stirred for 18 h at room temperature. The solvent was removed in vacuo to yield the title compound as a clear oil (100 mg, 100%). No further purification was attempted. LRMS+ve: 434 (M+1, 90%), 456 (M−1, 70%). HPLC: RT 6.2 min (95%).

Step C: N-hydroxy-N-[2R-(3-naphthalen-1-ylm-ethyl-ureido)-hexyl]-formamide

To a solution of N-benzyloxy-N-[2R-(3-naphthalen-1-ylmethyl-ureido)-hexyl]-formamide (100 mg, 0.43 mmol) in ethanol (6 ml) was added Pd/C (25% w/w, 15 mg) and one drop of formic acid and this suspension was then blanketed with hydrogen. The reaction mixture was stirred at room temperature for 18 h. The catalyst was filtered off and the solvent was removed under reduced pressure to yield an oil (77 mg). Preparative HPLC yielded the title compound as a clear oil (43 mg, 54%). HPLC: Rt 5.9 min (99%); LRMS, +ve ion 344 (M+1, 100%), 366 (M+Na, 80%); −ve ion 342 (M−1, 90%); $^1$H-NMR (CDCl$_3$) δ: 10.00 (1H, brs, OH), 8.14 (1H, s, CHO), 7.91 (1H, d, J=8.4 Hz, ArH), 7.81 (1H, d, J=7.9 Hz, ArH), 7.71 (1H, d, J=8.1 Hz, ArH), 7.53–7.45 (2H, m, ArH), 7.37–7.26 (2H, m, ArH), 5.71 (1H, brs, NH), 5.37 (1H, d, J=8.4 Hz, NH), 4.70 (2H, ddd, J=20.8 Hz, 15.1 Hz & 5.6 Hz), 4.06–4.01 (1H, m), 3.76 (1H, dd, J=13.5 Hz & 11.6 Hz), 1.77–1.65 (1H, m), 1.53–1.26 (6H, m), 0.8 (3H, J=7.0 Hz, m); $^{13}$C-NMR; δ(CDCl$_3$): 14.2, 22.8, 28.6, 32.2, 42.5, 47.1, 51.1, 123.5, 125.7, 125.8, 126.3, 126.8, 128.6, 129.2, 131.5, 134.2, 134.5, 160.6, 163.4.

The following compounds may also be prepared by the method of Example 1

1.
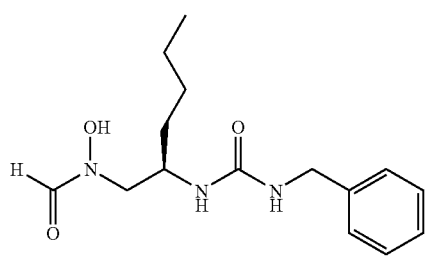

2.
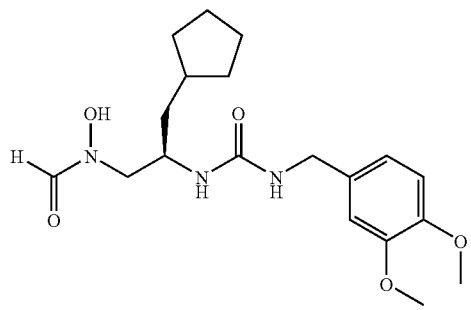

3.
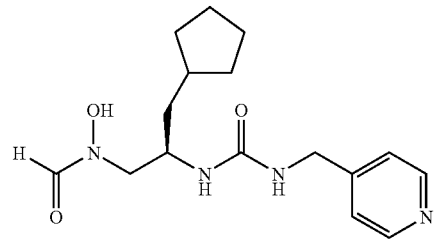

4.
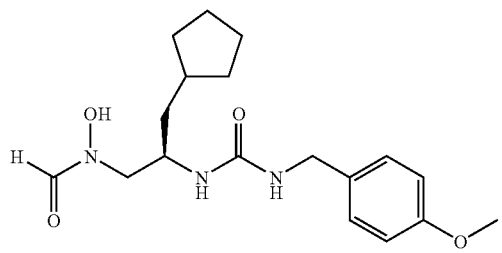

5.
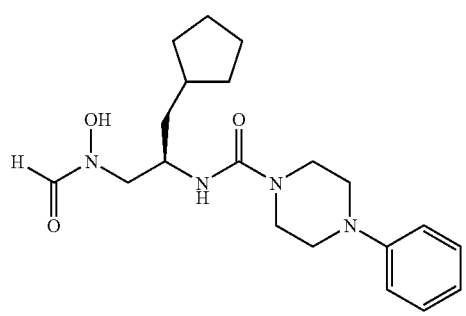

The invention claimed is:

1. A compound of formula (I), or a salt or hydrate thereof:

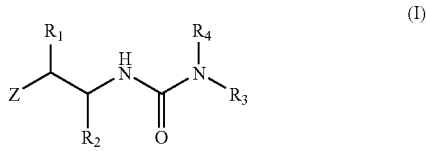

wherein:
Z represents a radical of formula —N(OH)CH(=O) or formula —C(=O)NH(OH);
R$_1$ represents hydrogen, methyl or trifluoromethyl or, except when Z is a radical of formula —N(OH)CH (=O), a hydroxy, halo or amino group
R$_2$ represents hydrogen or a group R$_{10}$—(D)$_n$—(ALK)$_m$— wherein
R$_{10}$ represents an optionally substituted C$_1$–C$_6$ alkyl, C$_2$–C$_6$ alkenyl, C$_2$–C$_6$ alkynyl, cycloalkyl, aryl, or heterocyclyl group and
ALK represents a straight or branched divalent C$_1$–C$_6$ alkylene, C$_2$–C$_6$ alkenylene, or C$_2$–C$_6$ alkynylene radical, and may be interrupted by one or more non-adjacent —NH—, —O— or —S— linkages,
D represents —NH—, —O— or —S—, and
n is 0 or 1;
R$_3$ and R$_4$ independently represent hydrogen or a group R$_{10}$(D)$_n$(ALK)$_m$— as defined for R$_2$, or R₃ and R₄ taken together with the nitrogen atom to which they are attached form an optionally substituted monocyclic heterocyclic ring containing from 5 to 7 ring atoms, one of which is the nitrogen atom to which R₄ and R₅ are attached and the remaining ring atoms being selected from compatible combinations of carbon, oxygen, sulfur and nitrogen.

2. A composition comprising a compound as claimed in claim 1 and a pharmaceutical acceptable carrier.

3. A compound as claimed in claim 1 wherein Z is a radical of formula —N(OH)CH(=O), and R₁ is hydrogen, methyl or trifluoromethyl.

4. A compound as claimed in claim 1 wherein Z is a radical of formula —C(=O)NH(OH), and R₁ is hydrogen, methyl, trifluoromethyl, hydroxy, halo or amino.

5. A compound as claimed in claim 1 wherein R₁ is hydrogen.

6. A compound as claimed in claim 3 wherein R₂ is:
   optionally substituted $C_1$–$C_8$ alkyl, $C_3$–$C_6$ alkenyl, $C_3$–$C_6$ alkynyl or cycloalkyl;
   phenyl($C_1$–$C_6$alkyl)-, phenyl($C_3$–$C_6$alkenyl)- or phenyl($C_3$–$C_6$alkynyl)- optionally substituted in the phenyl ring;
   cycloalkyl($C_1$–$C_6$alkyl)-, cycloalkyl($C_3$–$C_6$alkenyl)- or cycloalkyl($C_3$–$C_6$alkynyl)- optionally substituted in the cycloalkyl ring;
   heterocyclyl ($C_1$–$C_6$ alkyl)-, heterocyclyl ($C_3$–$C_6$ alkenyl)- or heterocyclyl($C_3$–$C_6$alkynyl)- optional substituted in the heterocyclyl ring; or
   $CH_3(CH_2)_pO(CH_2)_q$— or $CH_3(CH_2)_pS(CH_2)_q$—, wherein p is 0, 1, 2 or 3 and q is 1, 2 or 3.

7. A compound as claimed in claim 6 wherein R₂ is methyl, ethyl, n- or iso-propyl, n- and iso-butyl, n-pentyl, iso-pentyl 3-methyl-but-1-yl, n-hexyl, n-heptyl, n-octyl, methylsulfanylethyl, ethylsulfanylmethyl, 2-methoxyethyl, 2-ethoxyethyl, ethoxymethyl, 3-hydroxypropyl, allyl, 3-phenylprop-3-en-1-yl, prop-2-yn-1-yl, 3-phenylprop-2-yn-1-yl, 3-(2-chlorophenyl) prop-2-yn-1-yl, but-2-yn-1-yl, cyclopentyl, cyclohexyl, cyclopentylmethyl, cyclopentylethyl, cyclopentylpropyl, cyclohexylmethyl, cyclohexylethyl, cyclohexylpropyl, furan-2-ylmethyl, furan-3-ylmethyl, tetrahydrofuran-2-ylmethyl, tetrahydrofuran-2-ylmethyl, piperidinylmethyl, phenylpropyl, 4-chlorophenylpropyl, 4-methylphenylpropyl, 4-methoxyphenylpropyl, benzyl, 4-chlorobenzyl, 4-methylbenzyl, or 4-methoxybenzyl.

8. A compound as claimed in claim 6 wherein R₂ is ($C_1$–$C_6$)alkyl-, cycloalkylmethyl-, ($C_1$–$C_3$)alkyl-S—($C_1$–$C_3$)alkyl-, or ($C_1$–$C_3$)alkyl-O—($C_1$–$C_3$) alkyl-, especially n-propyl, n-butyl, n-pentyl, cyclopentylmethyl, cyclopentylethyl, cyclohexylmethyl or cyclohexylethyl.

9. A compound as claimed in claim 3 wherein R₃ is any of the R₂ groups specified in claim 6, 7, or 8.

10. A compound as claimed in claim 3 wherein R₃ is hydrogen.

11. A compound as claimed in claim 3 wherein R₄ is methyl, ethyl, n-or iso-propyl, n-or iso-butyl, n-pentyl, isopentyl, 3-methyl-but-1-yl, n-hexyl, n-heptyl, n-octyl, hydroxymethyl, 2-hydroxymethyl, methoxymethyl, 2-methoxyethyl, 2-ethoxyethyl, 2-ethoxymethyl, 3-hydroxypropyl, allyl, cyclopentyl, cyclohexyl, cyclopentylmethyl, cyclopentylethyl, cyclopentylpropyl, cyclohexylmethyl, cyclohexylethyl, cyclohexylpropyl, furan-2-ylmethyl, furan-3-methyl, tetrahydrofuran-2-ylmethyl, tetrahydrofuran-2-ylmethyl, piperidinyl, piperazinyl, piperidinylmethyl, piperazinylmethyl, phenyl, 4-chlorophenyl, 4-methylphenyl 4-methoxyphenyl, 4-hydroxyphenyl, 4-aminophenyl, benzyl, 4-chlorobenzyl, 4-methylbenzyl, 4-methoxybenzyl, 4-hydroxybenzy, 4-aminobenzyl, naphthyl, naphthylmethyl and naphthyl and naphthylmethyl substituted in the naphthyl rings by methyl, methoxy, hydroxy, chloro, or amino.

12. A compound as claimed in claim 3 wherein R₃ and R₄ taken together with the nitrogen to which they are attached form a piperidino, piperazino, morpholino, pyridyl, oxazolyl, thiazolyl, oxadiazolyl, or thiadiazolyl ring, any of which may be substituted.

* * * * *